United States Patent [19]

Allen

[11] 4,448,995
[45] May 15, 1984

[54] CATALYTIC HYDROGENATION OF DI(4-AMINOPHENYL)METHANE

[75] Inventor: Gary F. Allen, New Martinsville, W. Va.

[73] Assignee: Mobay Chemical Corporation, Pittsburgh, Pa.

[21] Appl. No.: 449,341

[22] Filed: Dec. 13, 1982

[51] Int. Cl.$^3$ ............................................. C07C 85/24
[52] U.S. Cl. ................................................... 564/451
[58] Field of Search ........................................ 564/451

[56] References Cited

U.S. PATENT DOCUMENTS

| | | | |
|---|---|---|---|
| 2,494,563 | 1/1950 | Kirk, Jr. et al. | 260/563 |
| 2,511,028 | 6/1950 | Whitman | 564/451 X |
| 2,606,924 | 8/1952 | Whitman | 260/563 |
| 2,606,925 | 8/1952 | Whitman | 260/563 |
| 2,606,928 | 8/1952 | Barkdoll et al. | 260/563 |
| 3,153,088 | 10/1964 | Arthur | 260/563 |
| 3,155,724 | 11/1964 | Arthur | 260/563 |
| 3,330,850 | 7/1967 | Campbell et al. | 260/453 |
| 3,347,917 | 10/1967 | Arthur | 260/563 |
| 3,361,814 | 1/1968 | Campbell et al. | 260/563 |
| 3,393,236 | 7/1968 | Koszewski | 260/563 |
| 3,557,180 | 1/1971 | Hoeschele | 260/453 |
| 3,590,002 | 6/1971 | Powers | 252/182 |
| 3,634,512 | 1/1972 | Poehler et al. | 564/451 |
| 3,636,108 | 1/1972 | Brake | 260/563 D |
| 3,644,522 | 2/1972 | Brake et al. | 260/563 D |
| 3,676,495 | 7/1972 | Hoeschele | 260/563 R |
| 3,697,449 | 10/1972 | Brake | 252/474 |
| 3,711,550 | 1/1973 | Brake | 260/563 B |
| 3,742,049 | 6/1973 | Komoto et al. | 260/563 D |
| 3,743,677 | 7/1973 | Grosskinsky et al. | 260/563 B |
| 3,766,272 | 10/1973 | Brake | 260/563 B |
| 3,825,586 | 7/1974 | Traumann | 260/501.2 |
| 3,914,307 | 10/1975 | Massie | 260/563 B |
| 3,959,374 | 5/1976 | Brennan et al. | 260/563 B |
| 4,161,492 | 7/1979 | Weissel | 260/563 R |
| 4,186,145 | 1/1980 | Weissel | 564/451 |
| 4,226,737 | 10/1980 | Kluger et al. | 252/182 |

FOREIGN PATENT DOCUMENTS 2125790  12/1972  Fed. Rep. of Germany ...... 564/451

*Primary Examiner*—Paul F. Shaver
*Attorney, Agent, or Firm*—Gene Harsh; Joseph C. Gil

[57] ABSTRACT

The present invention is directed to a process for the catalytic hydrogenation of di(4-aminophenyl)methane to a liquid di(4-aminocyclohexyl)methane containing from 15 to 40% by weight of the trans,trans isomer comprising hydrogenating di(4-aminophenyl)methane at a hydrogen pressure of at least 500 psi and at a temperature of from 100° to 300° C., in the presence of a ruthenium catalyst supported on an inert carrier, said catalyst being moderated with from 65 to 700% by weight, based on the weight of the ruthenium of a compound selected from the group consisting of nitrates and sulfates of alkali metals and alkaline earth metals.

10 Claims, No Drawings

CATALYTIC HYDROGENATION OF DI(4-AMINOPHENYL)METHANE

BACKGROUND OF THE INVENTION

In the production of di(4-aminocyclohexyl)methane by the catalytic hydrogenation of di(4-aminophenyl)methane, essentially three stereoisomers are formed.

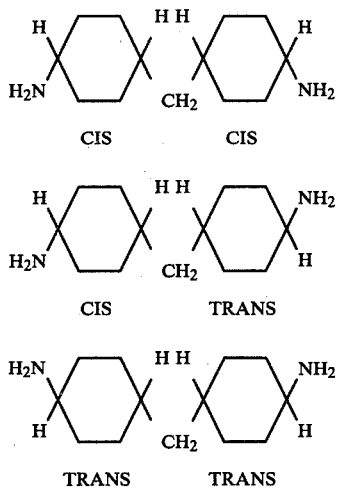

It is known in the art that in order to produce a corresponding isocyanate (via the known phosgenation process) which is liquid and storage stable at room temperature (i.e. from 20° to 25° C.), the mixture of amine stereoisomers used for phosgenation must contain the trans,trans stereoisomer in relatively narrow amounts (typically from 15 to 40% by weight, and preferably from 18.5 to 23.5% by weight).

Numerous techniques are known in the art for the production of amine mixtures containing the requisite amount of the trans,trans isomer. Typical of these known techniques are those described in U.S. Pat. Nos. 3,153,088; 3,155,724; 3,393,236; 3,644,522; 3,711,550 and 3,766,272. These known techniques generally require the separation of an amine mixture containing the requisite amount of the trans,trans isomer from an amine mixture formed after hydrogenation and containing around 50% by weight of the trans,trans isomer. Processes are known in the art for the production of a di(4-aminocyclohexyl)methane mixture containing the requisite amount of the trans,trans isomer directly from di(4-aminophenyl)methane without the need for an intermediate separation step (see e.g. U.S. Pat. No. 2,606,928); however, the rates of reaction are much too slow for commercial application.

Numerous processes are known in the art for the production of di(4-aminocyclohexyl)methane from di(4-aminophenyl)methane via catalytic hydrogenation using supported and unsupported ruthenium catalysts. Typical of these processes are those disclosed in U.S. Pat. Nos. 2,494,563; 2,606,924; 2,606,928; 2,606,925; 3,347,917; 3,644,522; 3,676,495; 3,959,374; 3,743,677; 3,914,307; 3,825,586; and 4,161,492. While some of these processes yield an amine mixture containing the trans,trans isomer in an amount necessary to allow for the production of an isocyanate which is liquid and storage stable at room temperature, the rates of reaction are much too slow for commercial use.

Ruthenium based catalysts have also been described as being useful in the hydrogenation of (a) polycycloaromatic polyamines formed from aniline and formaldehyde (see U.S. Pat. No. 4,226,737); (b) 2,4-bis(p-aminobenzyl) aniline (see U.S. Pat. No. 3,557,180); (c) 2,4'-diaminodiphenylmethane (see U.S. Pat. No. 3,590,002); (d) tolylene diamine/formaldehyde condensates (see U.S. Pat. Nos. 3,330,850 and 3,361,814); and (e) di(4-nitrophenyl) methane (see U.S. Pat. No. 3,742,049). However, none of these processes relate to the present problem, i.e., production of a di-(4-aminocyclohexyl)methane containing from 15 to 40% by weight of the trans,trans isomer.

Recently, processes have been developed for the direct hydrogenation of di(4-aminophenyl)methane to produce a liquid mixture of the stereoisomers of di(4-aminocyclohexyl) methane via utilization of a supported rhodium catalyst (U.S. application Ser. No. 269,199, filed June 1, 1981), an unsupported ruthenium dioxide catalyst (U.S. application Ser. No. 268,979, filed June 1, 1981), and a supported ruthenium catalyst (U.S. application Ser. No. 269,200, filed June 1, 1981). Although the resultant amine mixture is liquid and contains the requisite amount of trans,trans isomer, the economics of those processes are not commercially acceptable primarily due to low yield (i.e., less than 95%) because of by-product formation and due to short catalyst life.

Finally, it is known that the formation of tars, decomposition products and/or condensation products formed during the hydrogenation of di(4-aminophenyl)methane can be reduced and that such hydrogenation be seen repeatedly without catalyst rejuvenation, if the catalyst used is a supported ruthenium catalyst which has been alkali-moderated (see, e.g. U.S. Pat. Nos. 3,636,108 and 3,697,449). The materials described as being useful for such alkali-moderation are all very basic compounds and include basic alkali metal compounds such as (1) the hydroxides, carbonates, bicarbonates, methoxides, ethoxides, propoxides, t-butoxides, and other alkoxides of lithium, cesium, rubidium, sodium and potassium and (2) sodamide. Specific alkali materials described in the working examples of the two noted patents are sodium methoxide, sodium propoxide, potassium t-butoxide, lithium methoxide, sodamide, potassium hydroxide, sodium hydroxide, potassium methoxide, sodium ethoxide, sodium bicarbonate, cesium hydroxide, and rubidium hydroxide. Finally, the use of such alkali-moderated ruthenium catalysts to produce a material having a relatively high trans,trans content is also known (see U.S. Pat. No. 3,711,550).

DESCRIPTION OF THE INVENTION

A process has now been discovered which allows for the production of a liquid mixture of di(4-aminocyclohexyl)methane containing from 15 to 40% by weight, and preferably from 18.5 to 23.5% by weight of the trans,trans isomer. The discovery is based on the use of a supported ruthenium catalyst which has been treated with a nitrate or sulfate of an alkali or alkaline earth metal. The process is characterized by high yields, relatively low levels of half reduced amine and N-alkylation products, relatively low levels of polymeric-by-products and substantially improved performance in catalyst recycle reactions. Since all previously published works have used the alkali or alkaline salts of strong bases to moderate the catalyst, it was surprising to discover that the salts of strong acids were also effective in preventing side reactions.

The present invention is thus directed to a process for the catalytic hydrogenation of di(4-aminophenyl)methane to a liquid di(4-aminocyclohexyl)methane containing from 15 to 40% by weight and preferably 18.5 to 23.5% by weight, of the trans,trans isomer comprising hydrogenating di(4-aminophenyl) methane in the presence of a ruthenium catalyst supported on an inert carrier wherein the catalyst has been moderated with from 65 to 700% by weight, based on the weight of ruthenium, of a compound selected from the group consisting of nitrates and sulfates of alkali metals and alkaline earth metals, the hydrogenation being conducted at a hydrogen pressure of at least 500 psi and at a temperature of from 100° C. to 300° C.

The supported ruthenium catalysts are generally known in art and comprise elementary ruthenium deposited in a suitable inert carrier. Suitable inert carriers include carbon; calcium carbonate; rare earth oxides, such as cerium, praseodymium, or lanthanum; rare earth carbonates mixed rare earth oxide carbonates; alumina; barium sulfate; kieselguhr; pumice; diaspare; bauxite; periclase; zirconia; titania, diatomaceous earth; calcium sulfate; calcium oxide; barium oxide; barium carbonate; strontium carbonate, strontium oxide; strontium sulfate; silica; silica-alumina; etched nickel; or Nickrome and Inconel wire. The presently preferred carrier is alumina, and the presently preferred catalyst is available, for example, from Engelhard Corporation and comprises 5% by weight ruthenium on an alumina carrier.

Suitable alkali metal nitrates and sulfates include sodium nitrate, sodium sulfate, potassium sulfate, lithium sulfate, potassium nitrate, and lithium nitrate, while suitable alkaline earth metal nitrates and sulfates include magnesium nitrate, calcium nitrate, magnesium sulfate, calcium sulfate, barium sulfate, and barium nitrate. The presently preferred materials are lithium nitrate and magnesium nitrate, with the lithium nitrate being most preferred. The amount of metal nitrate added is generally from 65 to 700% by weight based on the weight of elementary ruthenium, and is preferably from 68 to 340% by weight.

Moderation can be accomplished by merely mixing the supported ruthenium catalyst either before or during the hydrogenation reaction or as a part of the catalyst preparation. The techniques described in U.S. Pat. Nos. 3,636,108 and 3,697,449 are eminently suitable for the moderation.

In conducting the process of the invention, the procedures commonly used in the art are employed. In general, the hydrogen pressure should be at least 500 psi, and will generally be from 2000 to 4000 psi. Of course, the pressures used are generally dependent on the equipment used. Thus, pressures of from 2000 to 8000 psi and higher can be used if suitable high pressure equipment is available. In general, it has been found that the yield will increase with increasing pressure. The hydrogenation is also generally conducted at a temperature of from 100° to 300° C., and preferably from 120° to 200° C. The exact choice of temperature in any given instance is a function of the reaction rate and the trans,-trans content desired. In general, the higher the temperature, the faster the reaction rate and the higher the trans,trans content of the final product. Thus, the temperatures will generally be selected to yield the best balance of reaction time and trans,trans content.

The hydrogenation is preferably carried out in the presence of an inert solvent, i.e., a solvent which does not substantially interfere with the desired course of the hydrogenation.

Useful solvents include ethers such as isopropyl ether or n-butyl ether; cyclohexane and other aliphatic hydrocarbons; alcohols such as butyl alcohol, methanol, ethanol, isopropanol, propanol and the like; and cyclic ethers such as tetrahydrofuran, dioxane, and the like. The amount of solvent used can range from 0 to 95% by weight based on the amount of amine and solvent. Preferably the amount of solvent used is such that the concentration of starting diamine in the reaction mixture is from about 30% to about 90% by weight based on the amount of amine and solvent. The presently preferred solvents are 2-propanol and tertiary butyl alcohol.

The catalyst is generally suspended in a solution of the starting diamine and the resulting suspension is subjected to hydrogenation in an appropriate hydrogenation vessel. The amount of catalyst employed is such that the amount of ruthenium metal present in the reaction mixture is at least 0.05% by weight and preferably within the range of about 0.1 to about 20% by weight based on the amount of starting diamine present in the reaction mixtures. As noted above, the amount of catalyst should be at least 0.05%. Economics generally dictate the upper limit since the catalyst is generally expensive. Preferably the quantity of catalyst employed is such that the amount of ruthenium present in the reaction mixture is within the range of from about 0.1 to about 5% by weight based on the amount of starting diamine employed.

Although not necessary to obtaining results of the present invention, if desired, ammonia can also be used as described in several of the patents noted above (see, e.g., U.S. Pat. Nos. 3,347,917; 3,636,108 and 3,644,522).

In general, the materials are mixed and added to the reactor in a batch process, but, of course, a continuous process could also be used.

The progress of the hydrogenation reaction is followed readily by observation of the amount of hydrogen taken up by the reaction mixture and the hydrogenation is terminated at the point at which the theoretical quantity of hydrogen has been absorbed. In general, under the conditions noted, the total hydrogenation time will not exceed about ninety minutes and will typically be from about 20 to 50 minutes. In the case of recycled catalysts the time may be as long as 75 minutes. Longer reaction times, particularly at higher temperatures, generally cause an increase in the trans,trans content. Following hydrogenation, the catalyst is separated from the solution of reduced material and the material is distilled to isolate the di(4-aminocyclohexyl)methane.

The invention is further illustrated, but is not intended to be limited by the following examples in which all parts and percentages are by weight unless otherwise specified.

EXAMPLE 1

232 Parts of an Engelhard ruthenium-on-alumina catalyst containing 5% ruthenium, 46 parts of lithium nitrate and 2500 parts of anhydrous isopropyl alcohol were added to a high pressure autoclave. 8700 Parts of molten di(4-aminophenyl)methane (MDA) were then added together with an additional 400 parts of isopropyl alcohol. The autoclave was then sealed and pressurized to 4000 psi of hydrogen and the contents were heated to 160° C. Both the temperature (to ±3° C.) and the pressure (to ±100 psi) were controlled. After hydrogen consumption stopped, the pressure and temperature were maintained for an additional 30 minutes (for a total reaction time of about 40 minutes). The contents of the autoclave were removed at room temperature and vacuum filtered. The product was found to contain about 23% by weight of the trans,trans isomer and amounted to a 93% yield as determined by HPLC.

EXAMPLES 2 THROUGH 13

5 Parts of the same ruthenium-on-alumina catalyst used in Example 1, 200 parts of di(4-aminophenyl)methane, 200 parts of 2-propanol and the amounts of moderator indicated in Table I were all charged to an autoclave. The moderators used, the reaction conditions and results were as indicated in TABLE I. All examples were run at 4000 psi. Examples 3, 4, 6, 7, 8 and 11 through 13 are comparative examples. The yield values were determined by HPLC while the other values were determined by GC or LC methods as indicated in TABLE I.

TABLE I

| Example | Moderator | PBW Moderator | Temp. °C. | Time Min. | % Yield LC | % t,t GC | % ½ Reduced MDA & N—iso-propyl by-products, GC | % Polymers LC |
|---|---|---|---|---|---|---|---|---|
| 2 | LiNO$_3$ | 2 | 160 | 26 | 98 | 22 | 2.5 | 2.4 |
| 3 | Li$_2$CO$_3$ | 0.5 | 175 | 19 | 72 | 29 | 3.5 | 26.8 |
| 4 | LiOH.H$_2$O | 2 | 175 | 18 | 91 | 34 | 4.3 | 8.8 |
| 5 | NaNO$_3$ | 1 | 160 | 63 | 100 | 28 | 3.9 | 5.1 |
| 6 | NaOH | 0.4 | 160 | 60 | 97 | 25 | 4.4 | 3.4 |
| 7 | Na$_2$CO$_3$ | 0.5 | 160 | 40 | 76 | 19 | 2.4 | 16.4 |
| 8 | NaOCH$_3$ | 0.4 | 170 | 26 | 90 | 26 | 4.5 | 6.9 |
| 9 | Mg(NO$_3$)$_2$ | 0.6 | 160 | 34 | 95 | 19 | None detected | 8.8 |
| 10 | Ba(NO$_3$)$_2$ | 0.6 | 160 | 38 | 77 | 21 | 2.3 | 18.6 |
| 11 | CaCO$_3$ | 0.5 | 160 | 40 | 73 | 20 | 2.2 | 18.8 |
| 12 | NH$_3$ | 16 | 185 | 15 | 91.8 | 40 | 4.2 | 5.1 |
| 13 | None | — | 185 | 14 | 71.7 | 43 | 14.7 | 19.7 |

EXAMPLE 14

In a manner similar to Example 1, 5 parts of the same ruthenium-on-alumina catalyst used in Example 1, 200 parts of t-butanol, 200 parts of di(4-aminophenyl)methane and 0.34 parts of sodium sulfate (Na$_2$SO$_4$) were charged to an autoclave. The autoclave was then sealed and pressurized to 4000 psi and the contents heated to 160° C. After hydrogen consumption stopped, the contents of the autoclave were removed and vacuum filtered. The product was found to contain about 25% by weight of the trans,trans isomer and amounted to a 97% yield as determined by HPLC.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the catalytic hydrogenation of di(4-aminophenyl)methane to a liquid di(4-aminocyclohexyl)methane containing from 15 to 40% by weight of the trans,trans isomer comprising hydrogenating di(4-aminophenyl)methane at a hydrogen pressure of at least 500 psi and at a temperature of from 100° to 300° C., in the presence of a ruthenium catalyst supported on an inert carrier, said catalyst being moderated with from 65 to 700% by weight, based on the weight of the ruthenium of a compound selected from the group consisting of nitrates and sulfates of alkali metals and alkaline earth metals.

2. The process of claim 1, wherein said liquid di(4-aminocyclohexyl)methane contains from 18.5 to 23.5% by weight of the trans,trans isomer.

3. The process of claim 1, wherein said catalyst is moderated with a compound selected from the group consisting of lithium nitrate and magnesium nitrate.

4. The process of claim 1, wherein said catalyst is moderated with from 68 to 340% by weight of said compound.

5. The process of claim 1, wherein said hydrogen pressure is from 2000 to 4000 psi.

6. The process of claim 1, wherein said temperature is from 120° to 200° C.

7. The process of claim 1, wherein the hydrogenation is conducted in the presence of from 0 to 95% by weight of an inert solvent, said percent by weight being based on the amount of starting amine and solvent.

8. The process of claim 7, wherein the amount of inert solvent is such that the concentration of starting diamine is from about 30 to about 90% by weight based on the amount of starting diamine and solvent.

9. The process of claim 7, wherein said solvent is selected from the group consisting of 2-propanol and tertiary butyl alcohol.

10. The process of claim 1, wherein the amount of catalyst employed is such that the amount of ruthenium metal present in the reaction mixture is at least 0.05% by weight based on the amount of starting diamine.

* * * * *